United States Patent
Aida et al.

(10) Patent No.: US 8,071,531 B2
(45) Date of Patent: Dec. 6, 2011

(54) FLAVOR AND FRAGRANCE COMPOSITION

(75) Inventors: Takashi Aida, Kanagawa (JP); Kenya Ishida, Kanagawa (JP)

(73) Assignee: Takasgo International Corporation, Tokyo (JP)

( * ) Notice: Subject to any disclaimer, the term of this patent is extended or adjusted under 35 U.S.C. 154(b) by 667 days.

(21) Appl. No.: 11/922,208

(22) PCT Filed: Jun. 20, 2006

(86) PCT No.: PCT/JP2006/312681
§ 371 (c)(1),
(2), (4) Date: Dec. 14, 2007

(87) PCT Pub. No.: WO2006/137556
PCT Pub. Date: Dec. 28, 2006

(65) Prior Publication Data
US 2009/0275669 A1    Nov. 5, 2009

(51) Int. Cl.
*A61Q 13/00* (2006.01)
*A61K 8/18* (2006.01)
*A61K 31/12* (2006.01)
*C07C 49/00* (2006.01)

(52) U.S. Cl. .......................... 512/23; 514/690; 568/376

(58) Field of Classification Search .................. None
See application file for complete search history.

(56) References Cited

U.S. PATENT DOCUMENTS

| | | | |
|---|---|---|---|
| 4,459,425 A | 7/1984 | Amano et al. | |
| 4,541,951 A | 9/1985 | Hall et al. | |
| 6,328,982 B1 * | 12/2001 | Shiroyama et al. | 424/401 |
| 2003/0149299 A1 * | 8/2003 | Borhan et al. | 562/544 |

FOREIGN PATENT DOCUMENTS

| | | |
|---|---|---|
| JP | 47-16647 | 9/1972 |
| JP | 47-16648 | 9/1972 |
| JP | 48-33069 | 5/1973 |
| JP | 58-88334 | 5/1983 |
| JP | 61-194049 | 8/1986 |
| JP | 2-290827 | 11/1990 |
| JP | 6-65023 | 3/1994 |
| JP | 7-82200 | 3/1995 |
| JP | 7-118119 | 5/1995 |

OTHER PUBLICATIONS

Suga et al., "Stereochemical Studies of Monoterpene Compounds V. The Rotational Conformation of the Acetyl Group of 10-Nor-8-oxomethols and 10-Nor-8-oxocarvomenthols," Bulletin of the Chemical Society of Japan, 1968, 4(5): pp. 1175-1179.*

* cited by examiner

*Primary Examiner* — Sreeni Padmanabhan
*Assistant Examiner* — Jody Karol
(74) *Attorney, Agent, or Firm* — McDermott Will & Emery LLP

(57) ABSTRACT

A flavor and fragrance composition with a cooling sensation effect comprising 1-(2-hydroxy-4-methylcyclohexyl)ethanone represented by the formula (1). The flavor and fragrance composition is added to a beverage or food product, a fragrance or cosmetic product, a daily utensil product, an oral composition, or a pharmaceutical product in the range of 0.0001 to 20% by weight to the total weight of the flavor and fragrance composition added.

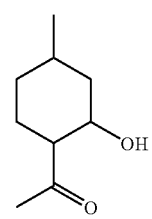

(1)

11 Claims, No Drawings

FLAVOR AND FRAGRANCE COMPOSITION

RELATED APPLICATIONS

This application is the U.S. National Phase under 35 U.S.C. §371 of International Application No. PCT/JP2006/312681, filed on Jun. 20, 2006, which in turn claims the benefit of Japanese Application No. 2005-180570, filed on Jun. 21, 2005, the disclosures of which Applications are incorporated by reference herein.

Technical Field

The invention relates to a flavor and fragrance composition comprising 1-(2-hydroxy-4-methylcyclohexyl)ethanone, and preferably to a flavor and fragrance composition having a cooling sensation effect comprising 1-(2-hydroxy-4-methylcyclohexyl)ethanone. The invention also relates to a beverage or food product, a fragrance or cosmetic product, a daily utensil product, an oral composition, or a pharmaceutical product having the flavor and fragrance composition compounded therein, and a method of producing the same.

Background Art

A substance that endows the skin, oral cavity, nose and throat of a person with a cool and refreshing feeling (cooling sensation), or a so-called cooling sensation agent, is used in various products such as toothpastes, confectioneries such as chewing gums and candies, tobacco, cataplasms, bath agents and cosmetics. L-menthol has been known as a representative cooling sensation agent and is widely used as a flavor and fragrance compound capable of providing a cool and refreshing feeling or a cooling sensation. However the cooling sensation effect thereof does not last so long and when a large amount of 1-menthol is used for imparting the enhanced cooling sensation effect, it may give a bitter taste.

Many compounds having a cooling sensation effect other than 1-menthol have been conventionally proposed. Examples of such compounds include 3-substituted p-menthane (see JP47-16647 A), N-substituted p-menthane-3-carboxamide (see JP47-16648 A), 1-menthyl glycoside (see JP 48-33069 A), 3-(1-menthoxy)propane-1,2-diol (see JP 58-88334 A), 1-menthyl-3-hydroxybutylate (see JP 61-194049 A), 1-alkoxy-3-(1-menthoxy)propane-2-ol (see JP 2-290827 A), esters of 3-hydroxymethyl-p-menthnane (see JP 5-255186 A), methyl N-acetylglycine menthanate (see JP 5-255217 A), (−)-isopulegol (see JP 6-65023 A), (2S)-3-{(1R,2S,5R-[5-methyl-2-(1-methylethyl)cyclohexyl]oxy}-1,2-propanediol (see JP 7-82200 A), and 2-hydroxymethyl menthol (see JP 7-118119 A).

On the other hand, it has been reported that 1-(2-hydroxy-4-methylcyclohexyl)ethanone can be synthesized by several methods, and that it is important as an intermediate of pharmaceuticals and a synthetic intermediate of flavor and fragrance products (see US 2003-149299 A). However, it has not been reported that notes of the flavor and fragrance composition are confirmed with respect to 1-(2-hydroxy-4-methylcyclohexyl)ethanone. Therefore any use of it as the flavor and fragrance composition has been unknown. Further it has not been reported any verification of sensory stimulating effects such as cooling effect with respect to 1-(2-hydroxy-4-methylcyclohexyl)ethanone.

DISCLOSURE OF THE INVENTION

Problem to be Solved by the Invention

As described above, many compounds having the cooling sensation effect have been proposed. Although these compounds show the cooling sensation effect in their own way, the compounds do not show so satisfactory property with respect to at least any one of the strength of cooling sensation, lasting of the cooling sensation effect, odor, and taste. Accordingly, the flavor and fragrance composition containing these compounds having the cooling sensation effect has also involved the same problem. Conventionally, a warming and/or pungent agent composition having an enhanced warming and/or pungent sensation effect have been obtained by adding the cooling sensation agent to the warming and/or pungent substance composition. In this case also, the flavor and fragrance composition containing the warming and/or pungent agent composition having an excellent warming and/or pungent sensation effect with no malodor and bitter taste originating from the cooling sensation agent is desired.

Accordingly, an object of the invention is to provide a flavor and fragrance composition having no problem described above. That is, the object of the invention is to provide a flavor and fragrance composition having a strong cooling sensation effect and excellent lasting effect of a cool and refreshing feeling and a cooling sensation without any stimulating sensation, malodor, and bitter taste originating from the cooling sensation agent when it is used for obtaining the cooling sensation effect. And the object of the invention is also to provide a flavor and fragrance composition not only having a strong cooling sensation effect and excellent lasting effect of a cool and refreshing feeling but also imparting a high flavor and fragrance quality-improving effect to the products, with which the fragrance and flavor composition with properties of enhanced emission of fragrance and excellent remaining fragrance, is compounded.

Another object of the invention is to provide a beverage or food product, a fragrance or cosmetic product, a daily utensil product, an oral composition, or a pharmaceutical product with an excellent cool and refreshing feeling effect, cooling sensation effect and lasting effect thereof and further given a flavor and fragrance quality-improved effect by compounding with the flavor and fragrance composition, and to provide a method of producing the products.

A different object of the invention is to provide a flavor and fragrance composition having an enhanced warming and/or pungent sensation effect by addition of cooling sensation agent, and further to provide a flavor and fragrance composition having an enhanced warming and/or pungent sensation effect and improved emission and remaining of flavor and fragrance.

A further different object of the invention is to provide a flavor and fragrance composition having an improved warming and/or pungent sensation effect and further being able to impart a high flavor and fragrance quality-improving effect to various products by adding the flavor and fragrance composition thereto.

A further different object of the invention is to provide a beverage or food product, a fragrance or cosmetic product, a daily utensil product, an oral composition, or a pharmaceutical product to which a high flavor and fragrance quality-improved effect is imparted by compounding with the flavor and fragrance composition having an improved warming and/or pungent sensation effect, and to provide a method of producing the products.

An object of the invention according to a different point of view of the invention is, in addition to the objects described above, to provide a cooling sensation agent composition excellent in strength of a cool and refreshing feeling and a cooling sensation with a good lasting property without any stimulating sensation, malodor and bitter taste, to provide a warming and/or pungent substance composition having an enhanced warming and/or pungent sensation effect by adding the cooling sensation agent composition, and to provide a sensory stimulant agent composition having compounded therein the cooling sensation agent composition or warming and/or pungent agent composition.

Means for Solving Problem

The inventors have made intensive studies on the cooling sensation effect of various compounds derived from 1-menthol and related compounds for solving the problems as described above. As a result, the inventors have found that 1-(2-hydroxy-4-methylcyclohexyl)ethanone represented by the following formula (1) has a strong cooling sensation effect with a good lasting property and without any problems of a stimulating sensation, malodor and bitter taste, therefore the compound is useful as a cooling sensation agent. The inventors have also found that 1-(2-hydroxy-4-methylcyclohexyl)ethanone can moderate the stimulating odor inherent in 1-menthol when 1-menthol is used as a cooling sensation substance, the cooling sensation effect can be enhanced by combining it with other cooling sensation substances except 1-menthol, and the warming and/or pungent sensation effect can be improved by adding it to a warming and/or pungent substance. It has also been found that a cooling sensation effect excellent in the lasting property, emission of fragrance and remaining of fragrance are imparted to a flavor and fragrance composition by addition of 1-(2-hydroxy-4-methylcyclohexyl)ethanone and further a high flavor and fragrance quality-improving effect is imparted to various products flavored and fragrance-added with the flavor and fragrance composition. The invention has been completed based on the finding as described above.

The inventions are as following.

1. A flavor and fragrance composition consisting of or comprising 1-(2-hydroxy-4-methylcyclohexyl)ethanone represented by the formula (1):

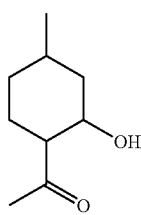

(1)

2. The flavor and fragrance composition according to item 1, wherein the 1-(2-hydroxy-4-methylcyclohexyl)ethanone represented by the above formula (1) is a (1R,2R,4R)-stereoisomer compound represented by the following formula (1-a):

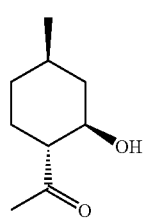

(1-a)

3. The flavor and fragrance composition according to item 1 or 2, wherein the flavor and fragrance composition has a cooling sensation effect.

4. The flavor and fragrance composition according to any one of items 1 to 3, further comprising at least one of cooling sensation substances not included in the compounds represented by the above formula (1).

5. The flavor and fragrance composition according to item 4, wherein the cooling sensation substances not included in the compounds represented by the above formula (1) are menthol, menthone, camphor, pulegol, isopulegol, cineol, mint oil, peppermint oil, spearmint oil, eucalyptus oil, 3-1-menthoxypropane-1,2-diol, N-alkyl-p-menthane-3-carboxamide, 3-1-menthoxy-2-methylpropane-1,2-diol, p-menthane-3,8-diol, 2-1-menthoxyethane-1-ol, 3-1-menthoxypropane-1-ol, 4-1-menthoxybutane-1-ol, menthyl 3-hydroxybutanoate, menthyl lactate, menthone glycerin ketal, 2-(2-1-menthyloxyethyl)ethanol, menthyl glyoxylate, N-methyl-2,2-isopropylmethyl-3-methylbutanamide, menthyl 2-pyrrolidone-5-carboxylate, monomenthyl succinate, alkali metal salts of monomenthyl succinate, and alkali earth metal salts of monomenthyl succinate, monomenthyl glutarate, alkali metal salts of monomenthyl glutarate, alkali earth metal salts of monomenthyl glutarate, N-[[5-methyl-2-(1-methylethyl)cyclohexyl]carbonyl]glycine, p-menthane-3-carboxylic acid glycerol ester, Menthol propylene glycol carbonate; Menthol ethylene glycol carbonate, and 6-isopropyl-3,9-dimethyl-1,4-dioxaspiro[4.5]decan-2-one.

6. The flavor and fragrance composition according to any one of items 1 to 5, further comprising at least one of warming and/or pungent substances.

7. The flavor and fragrance composition according to item 6, wherein the warming and/or pungent substances are vanillylethyl ether, vanillylpropyl ether, vanillin propylene glycol acetal, ethylvanillin propylene glycol acetal, capsaicin, gingerol, vanillylbutyl ether, vanillylbutyl ether acetate, 4-(1-menthoxymethyl)-2-phenyl-1,3-dioxolane, 4-(1-menthoxymethyl)-2-(3',4'-dihydroxyphenyl)-1,3-dioxolane, 4-(1-menthoxymethyl)-2-(2'-hydroxy-3'-methoxyphenyl)-1,3-dioxolane, 4-(1-menthoxymethyl)-2-(4'-methoxyphenyl)-1,3-dioxolane, 4-(1-menthoxymethyl)-2-(3',4'-methylenedioxyphenyl)-1,3-dioxolane, 4-(1-methoxymethyl)-2-(3'-methoxy-4'-hydroxyphenyl)-1,3-dioxolane, red pepper oil, red pepper oleoresin, ginger oleoresin, nonylic acid vanillamide, jambu oleoresin, Japanese pepper extract, sanshool-I, sanshool-II, sanshoamide, black pepper extract, chavicine, piperine, and spilanthol.

8. A beverage or food product, a fragrance or cosmetic product, a daily utensil product, an oral composition, or a pharmaceutical product, wherein 0.0001 to 20% by weight of the flavor and fragrance composition according to any one of items 1 to 7 is compounded.

9. A method of producing a beverage or food product, a fragrance or cosmetic product, a daily utensil product, an oral composition, or a pharmaceutical product, wherein the flavor and fragrance composition according to any one of items 1 to 7 is added to the beverage or food product, fragrance or cosmetic product, daily utensil product, oral composition, or pharmaceutical product.

10. A kit comprising a sports rub gel or cream, said sports rub gel or cream comprising a composition of any one of the preceding items 1 to 9.

11. A kit comprising a shaving gel or cream, said shaving gel or cream comprising a composition of any one of items 1 to 9.

12. A kit comprising a personal care product, said personal care product comprising a composition of any one of items 1 to 9.

13. A method of relieving sore muscles comprising topically applying a composition of any one of items 1 to 9.

14. A method of preparing a topical medicine or topical analgesic lotion cream or spray comprising adding the composition of any one of items 1 to 9 to a biologically active agent.

15. A method of increasing the effect of one or more sensate materials contained in a composition comprising adding an effective amount of 1-(2-hydroxy-4-methylcyclohexyl)ethanone to the composition containing the sensate materials.

16. The composition of any one of items 1 to 9, wherein the composition is in a form suitable for topical delivery.

EFFECTS OF THE INVENTION 1-(2-hydroxy-4-methylcyclohexyl)ethanone used in the flavor and fragrance composition of the invention shows no stimulating sensation, malodor and bitter taste, is able to impart a cool and refreshing feeling and a cooling sensation to various products such as beverage or food products, fragrance or cosmetic products, toiletry products, bath agents and pharmaceutical products by addition to these products, and is able to provide the products excellent in lasting of the cool and refreshing feeling and cooling sensation. 1-(2-hydroxy-4-methylcyclohexyl)ethanone used in the flavor and fragrance composition of the invention or compounded in beverage or food products, fragrance or cosmetic products, daily utensil products, oral compositions and pharmaceutical products of the invention exhibits excellent properties that it causes hardly a skin stimulating sensation that is not preferable for the human body and is excellent in storage stability without coloring. The flavor and fragrance composition comprising 1-(2-hydroxy-4-methylcyclohexyl)ethanone is excellent in lasting of the cool and refreshing feeling and cooling sensation and shows enhancing diffusivity and long-lasting property of the flavor and fragrance composition, and thereby imparts a high flavor and fragrance quality-improving effect to the products flavored and fragrance-added with the flavor and fragrance composition too. For example, 1-(2-hydroxy-4-methylcyclohexyl)ethanone, particularly, (1R,2R,4R)-1-(2-hydroxy-4-methylcyclohexyl)ethanone has acetophenone-like odor with a sweet scent. Examples of the flavor and fragrance quality-improving effect on various products include as following. That is, soft sweetness or mild sensation of a peach can be restored by adding (1R,2R,4R)-1-(2-hydroxy-4-methylcyclohexyl)ethanone to a peach flavor; a mild and mellow sensation can be given to a green tea flavor by adding (1R,2R,4R)-1-(2-hydroxy-4-methylcyclohexyl)ethanone to the green tea flavor and sweet scent of the green tea can be restored thereby; or a soft sweetness can be given to a black tea flavor by adding (1R,2R,4R)-1-(2-hydroxy-4-methylcyclohexyl)ethanone to the black tea flavor and a mild sensation of the black tea can be restored thereby. Moreover, by flavoring the tobacco with (1R,2R,4R)-1-(2-hydroxy-4-methylcyclohexyl)ethanone, mild feeling was imparted to the smoke from the tobacco and a tobacco-like flavor or a emphatic tobacco-like flavor can be also imparted to the tobacco thereby.

DESCRIPTION OF THE PREFERRED EMBODIMENTS

The invention will be described in more detail below. 1-(2-hydroxy-4-methylcyclohexyl)ethanone represented by the above formula (1) and used in a flavor and fragrance composition of the invention may be either a racemic compound or an optically active substance. Preferable examples of the optically active substance include a (1R,2R,4R)-compound, i.e., the compound represented by the formula (1-a) above.

1-(2-hydroxy-4-methyl cyclohexyl)ethanone of the invention represented by formula (1) is a known compound as described above, and can be produced by, for example, ozone oxidation of commercially available isopulegol. The (1R,2R,4R)-compound of 1-(2-hydroxy-4-methylcyclohexyl)ethanone represented by the formula (1-a) is obtained by the method described above.

1-(2-hydroxy-4-methylcyclohexyl)ethanone of the formula (1) or (1R,2R,4R)-1-(2-hydroxy-4-methylcyclohexyl)ethanone of the formula (1-a) of the invention is a compound having a strong and lasting cooling sensation effect, and it may be used as a cooling sensation agent composition by itself.

The application range and application method of 1-(2-hydroxy-4-methylcyclohexyl)ethanone obtained in the invention should be appropriately changed depending on the kinds of products and the purpose of use. However, 1-(2-hydroxy-4-methylcyclohexyl)ethanone is preferably compounded in the range from 0.0001 to 90% by weight to the total weight of the composition for the flavor and fragrance composition; or preferably compounded in a proportion of about $1 \times 10^{-7}\%$ by weight or more, usually in the range from 0.0001 to 20% by weight, and particularly in the range from 0.001 to 5% by weight, of the total weight of the composition for products such as a beverage or food product, a fragrance or cosmetic product, a daily utensil product, an oral composition, and a pharmaceutical product.

In the invention, a cooling sensation agent composition enhanced in strength of the cooling sensation may be prepared by using at least one component selected from cooling sensation substances not included in 1-(2-hydroxy-4-methylcyclohexyl)-ethanone represented by the formula (1) in combination with 1-(2-hydroxy-4-methylcyclohexyl)ethanone of the formula (1).

The cooling sensation substance not included in 1-(2-hydroxy-4-methylcyclohexyl)ethanone represented by the formula (1) may be any cooling sensation substances including cooling sensation substances well known or known in the art so long as it is a substance having a cooling sensation effect and is not particularly limited. Examples of the substance not included in 1-(2-hydroxy-4-methylcyclohexyl)ethanone represented by the formula (1) include menthol, menthone, camphor, pulegol, isopulegol, cineol mint oil, peppermint oil, spearmint oil, eucalyptus oil, 3-1-menthoxypropane-1,2-diol, N-alkyl-p-menthane-3-carboxamide, 3-1-menthoxy-2-methylpropane-1,2-diol, p-menthane-3,8-diol, 2-1-menthoxyethane-1-ol, 3-1-menthoxy propane-1-ol, 4-1-menthoxybutane-1-ol, menthyl 3-hydroxybutanoate, menthyl lactate, menthone glycerin ketal, 2-(2-1-menthyloxyethyl)ethanol, menthyl glyoxylate, N-methyl-2,2-isopropylmethyl-3-methyl butanamide, menthyl 2-pyrrolidone-5-carbonate, monomenthylsuccinate, alkali metal salts of monomenthyl succinate, alkali earth metal salts of monomenthyl succinate, monomenthyl glutarate, alkali metal salts of monomenthyl glutarate, alkali earth metal salts of monomenthyl glutarate, N-[[5-methyl-2-(1-methylethyl)cyclohexyl]carbonyl]glycine, p-menthane-3-carboxylic acid glycerol ester, Menthol propylene glycol carbonate; Menthol ethylene glycol carbonate, and 6-isopropyl-3,9-dimethyl-1,4-dioxaspiro[4.5]decan-2-one. These compounds may be used alone, or by appropriately compounding two or more of them. When 1-menthol is used as the other cooling sensation substances, the cooling sensation effect is enhanced as described above, and further, the stimulative odor of 1-menthol is softened by using 1-(2-hydroxy-4-methylhexyl)ethanone. Accordingly, the use of 1-(2-hydroxy-4-methylhexyl)ethanone with 1-menthol is one of preferable aspects of the invention.

1-(2-hydroxy-4-methylcyclohexyl)ethanone and the cooling sensation substance not included therein may be used in any ratio in the range wherein the effect of the invention is not impaired. The weight ratio between 1-(2-hydroxy-4-methylcyclohexyl)ethanone and the cooling sensation substance not included therein is preferably in the range from 1:99 to 70:30.

Since the cooling sensation agent composition described above has a strong and long-lasting cooling sensation effect, a sensory stimulant composition having a cooling sensation effect can be prepared by addition of the cooling sensation agent composition in the invention.

When the sensory stimulant composition having a cooling sensation effect of the invention is prepared, the amount of the cooling sensation agent composition compounded should be appropriately changed depending on the kind of the product and the purpose of use together with the application range and application method, and it is preferable to use the cooling sensation agent composition usually in a concentration range from 0.0001 to 20% by weight, particularly from 0.001 to 5% by weight, to the total weight of the sensory stimulant composition.

The cooling sensation agent composition of the invention consisting of 1-(2-hydroxy-4-methylcyclohexyl)ethanone or comprising 1-(2-hydroxy-4-methylcyclohexyl)ethanone may be prepared into a cooling sensation agent composition or a sensory stimulant composition having an enhanced cooling sensation effect, or into a warming and/or pungent agent composition or a sensory stimulant composition having an enhanced warming and/or pungent sensation effect by using a warming and/or pungent substance together.

The warming and/or pungent substance may be any substance including warming and/or pungent substances well known or known in the art so long as it is a substance having a warming and/or pungent effect, and is not particularly limited. Examples thereof include vanillylethylether, vanillylpropyl ether, vanillin propyleneglycol acetal, ethylvanillin propylene glycol acetal, capsaicin, gingerol, vanillyl butyl ether, vanillyl butyl ether acetate, 4-(1-menthoxymethyl)-2-phenyl-1,3-dioxolane, 4-(1-menthoxymethyl)-2-(3',4'-dihydroxyphenyl)-1,3-dioxolane, 4-(1-menthoxymethyl)-2-(2'-hydroxy-3'-methoxyphenyl)-1,3-dioxolane, 4-(1-menthoxymethyl)-2-(4'-methoxyphenyl)-1,3-dioxolane, 4-(1-menthoxymethyl)-2-(3',4'-methylenedioxyphenyl)-1,3-dioxolane, 4-(1-methoxymethyl)-2-(3'-methoxy-4'-hydroxyphenyl)-1,3-dioxolane, red pepper oil, red pepper oleoresin, ginger oleoresin, nonylic acid vanillamide, jambu oleoresin, Japanese pepper extract, sanshool-I, sanshool-II, sanshoamide, black pepper extract, chavicine, piperine, and spilanthol. These substances may be used singly, or as a mixture of two or more thereof by appropriately compounding ratio.

The compounding ratio of the warming and/or pungent substance and the cooling sensation substance may be in the range wherein the warming and/or pungent sensation effect is not imparted to the cooling sensation agent composition compounded with the warming and/or pungent substance when the object of compounding is to enhance the cooling sensation effect. The amount of the warming and/or pungent substance compounded is usually from 0.001 to 0.95 times, preferably from 0.01 to 0.5 times, of the total amount of the cooling sensation agent composition according to the invention. At this time, the cooling sensation effect of the cooling sensation agent composition is further improved by adding the warming pungent sensation substance to the cooling sensation agent composition in the ratio as described above.

The proportion of use of the cooling sensation agent composition in the invention may be in the range wherein the cooling sensation effect is not imparted to the warming and/or pungent substance composition compounded with the cooling sensation agent when the object of adding the cooling sensation agent composition is to enhance the warming and/or pungent sensation effect. The amount of the cooling sensation agent compounded is usually from 0.001 to 0.95 times, preferably from 0.01 to 0.5 times, of the total amount of the warming and/or pungent substance.

The flavor and fragrance composition of the invention is featured in containing 1-(2-hydroxy-4-methylcyclohexyl)ethanone, and the composition may include any compositions or may be produced by any compounding methods so long as it contains 1-(2-hydroxy-4-methylcyclohexyl)ethanone. For example, the flavor and fragrance composition comprising 1-(2-hydroxy-4-methylcyclohexyl)ethanone may be prepared by being directly mixed with other components for forming the flavor and fragrance composition, or by preparing a cooling sensation agent composition containing 1-(2-hydroxy-4-methylcyclohexyl)ethanone as a constituent, followed by mixing the composition with other components for forming the flavor and fragrance composition. Otherwise, the flavor and fragrance composition may be formulated into a warming and/or pungent substance composition or sensory stimulant composition first, followed by mixing the composition with other components for forming the flavor and fragrance composition. Alternatively, a base flavor and fragrance composition is prepared in advance by mixing flavor and fragrance components, and then the cooling sensation agent composition consisting of 1-(2-hydroxy-4-methylcyclohexyl)ethanone, or cooling sensation agent composition, warming and/or pungent substance composition or sensory stimulant composition containing 1-(2-hydroxy-4-methylcyclohexyl)ethanone may be compounded in the base flavor and fragrance composition prepared in advance as described above.

In the flavor and fragrance composition of the invention, there are exemplified various aroma chemicals, natural essential oils, natural aroma chemicals, citrus oils and animal aroma chemicals as other flavor and fragrance components to be mixed with the cooling sensation agent composition consisting of 1-(2-hydroxy-4-methylcyclohexyl)ethanone or with the cooling sensation agent composition, warming and/or pungent substance composition or sensory stimulant composition containing 1-(2-hydroxy-4-methylcyclohexyl)ethanone. Flavor and fragrance components suitable for formulating desired flavor and fragrance compositions in the invention may be appropriately selected from a variety of flavor and fragrance components described in, for example, Shu-chi/Kanyoh Gijutsu Shuh (Collection of Known and Customary Technologies)—Flavoring and Fragrance Materials—, Part I, Jan. 29, 1999, published by Japan Patent Office. Representative examples of the flavoring and fragrance components include α-pinene, limonene, cis-3-hexenol, phenylethyl alcohol, styralyl acetate, eugenol, methyl dihydrojasmonate, rose oxide, linalool, benzaldehyde, muscone, MUSK T (manufactured by TAKASAGO INTERNATIONAL CORPORATION), Thesaron (Manufactured by TAKASAGO INTERNATIONAL CORPORATION), orange oil, capsicum oleoresin, vanilla extract, isoamyl acetate, ethyl butylate, ethyl 2-methylbutylate, ethyl caproate, allyl caproate, γ-decalactone and vanilline.

The contents of the cooling sensation agent composition, warming and/or pungent substance composition and sensory stimulant composition containing 1-(2-hydroxy-4-methylcyclohexyl)ethane in the flavor and fragrance composition of the invention are different depending on various conditions such as the kinds of the flavoring and fragrance materials and other components compounded together therewith and the aspect or purpose of use of the composition, for example, whether the composition is used for imparting a cooling sensation effect or warming and/or pungent sensation effect to the product. However, the content may be in any range capable of attaining the desired effect. For example, in the fragrance composition, the content is generally from 0.001 to 50% by weight, particularly preferably from 0.01 to 20% by weight, relative to the total weight of the fragrance composition. And in the flavor composition, the content is preferably in general in the range from 0.0001 to 50% by weight, more preferably from 0.001 to 30% by weight relative to the total weight of the flavor composition.

The flavor and fragrance composition of the invention may contain one or two or more of other flavor and fragrance retaining agents usually used for the flavor and fragrance composition, if necessary. Examples of the flavor and fragrance retaining agents include ethylene glycol, propylene glycol, dipropylene glycol, glycerin, hexylene glycol, benzyl benzoate, triethyl citrate, diethyl phthalate, Hercolyn, medium-chain fatty acid triglyceride, medium-chain fatty acid diglyceride, 3-1-menthoxypropane-1,2-diol, 3-1-memthoxy-2-methylpropane-1,2-diol and p-menthane-3,8-diol. The composition may contain one of them, or two or more of them.

In the invention, the cooling sensation agent composition, warming and/or pungent agent composition and sensory stimulant composition are used for imparting cooling sensation, warming and/or pungent sensation or sensory stimulating sensation to various products as the respective compositions alone or as a flavor and fragrance composition containing any one of these compositions. As the products capable of being endowed with the cooling sensation, warming and/or pungent sensation or sensory stimulating sensation accompanying the cooling sensation or warming and/or pungent sensation by the flavor and fragrance composition of the invention, or by the cooling sensation agent composition, warming and/or pungent agent composition or sensory stimulant composition of the invention, there are exemplified beverage or food products, fragrance or cosmetic products, daily utensil products, oral compositions, and pharmaceutical products.

Examples of the beverage or food products of the invention capable of being endowed with the cooling sensation, warming and/or pungent sensation, or sensory stimulating sensation accompanying the cooling sensation or warming and/or pungent sensation by the flavor and fragrance composition, or by the cooling sensation agent composition, warming and/or pungent agent composition or sensory stimulant composition include beverages such as fruit beverages, fruit spirits, milk-based drinks, carbonated drinks, soft drinks and health and nutrient drinks; frozen deserts such as ice creams, sherbets and popsicles; deserts such as jelly and puddings; confectionary such as cakes, cookies, chocolates and chewing gums; Japanese sweets such as bean-jam buns, thick jellied sweet made of azuki bean paste and thick jellied sweet made of powdered rice paste; jams; candies; breads; tea drinks and other favorite drinks such as green tea, oolong tea, black tea, persimmon leaf tea, chamomile tea, sasa veitchii tea, mulberry leaf tea, Houttuynia cordata tea, puaar tea, mate tea, rooibos tea, gymnema tea, guava tea, coffee and cocoa; soups such as Japanese style soups, Western style soups and Chinese style soups; flavor seasonings; various instant drinks and foods; various snacks; and oral products.

Examples of the fragrance or cosmetic products or daily utensil products and groceries of the invention capable of being endowed with the flavor an fragrance composition, or with the cooling sensation agent composition, warming and/or pungent agent composition or sensory stimulant composition include fragrance products, skin-care cosmetics, make-up cosmetics, hair cosmetics, anti-sunburn cosmetics, medicinal cosmetics, hair-care products, soaps, body lotions, bath utensils, detergents, soft finishing agents, cleaning agents, kitchen detergents, breaching agents, aerosol agents, deodorant-aromatics, repellents, tobacco and other groceries.

More specifically, the examples include:

perfume, Eau de Perfum, Eau de Toilette, and Eau de Cologne as the fragrance products;

face washing cream, vanishing cream, cleansing cream, cold cream, massage cream, milky lotion, skin lotion, beauty wash, beauty pack, and make-up remover as skin-care cosmetics;

foundation, face powder, pressed powder, talcum powder, rouge, lip stick, lip cream, cheek rouge, eye liner, mascara, eye shadow, eyebrow-color, eye pack, nail enamel, and enamel remover as make-up cosmetics; and pomade, brilliantine, set lotion, hair stick, hair solid, hair oil, hair treatment, hair cream, hair tonic, hair liquid, hair spray, bandlin, hair-growing agent, and hair dye as hair cosmetics.

Examples of the anti-sunburn cosmetics include suntan products and sunscreen products;

examples of the medicinal cosmetics include antiperspirant, after-shaving lotion and gel, permanent wave agent, medicinal soap, medicinal shampoo, and medicinal skin-care cosmetics.

Examples of the hair-care products include shampoo, rinse, rinse-in-shampoo, hair conditioner, hair treatment, and hair pack;

examples of the soaps include toilet soap, bath soap, perfume soap, clear soap, and synthetic soap;

examples of the body cleaners include body soap, body shampoo, and hand soap;

examples of the bath utensils include bath agent such as bath salt, bath tablet and bath liquid, foam bath such as bubble bath, bath oil such as bath perfume and bath capsule, milk bath, bath jelly, and bath cube; and examples of the detergents include heavy detergent for clothes, light detergent for clothes, liquid laundry detergent, laundry soap, compact detergent, and powder detergent.

Examples the soft finishing agents include softener and furniture care;

examples of the cleaning agents include cleanser, house wash, toilet cleaner, bath cleaner, glass cleaner, fungicide, and cleaner for drain pipe;

examples of the kitchen detergents include kitchen soap, kitchen synthetic soap, and dish wash;

examples of the bleaching agents include oxidant bleach such as chlorine bleach and oxygen bleach, reductive bleach such as sulfur containing bleach, and optical bleach;

examples of the aerosol agents include spray type aerosol and powder spray;

examples of the deodorant-aromatics include solid, gel and liquid deodorizer and aromatics; and examples of the groceries include tissue paper and toilet paper.

Examples of the oral compositions include toothpaste, mouth cleaner, mouth wash, troche, and chewing gum; and examples of the medical products include external use medicines such as cataplasm and ointment, and internal medicines.

In the invention when the cooling sensation agent composition, warming and/or pungent agent composition and sensory stimulant composition, and the flavor and fragrance composition containing these compositions are used for endowing above various products with cooling sensation, warming and/or pungent sensation or sensory stimulating sensation, each component maybe directly added to or compounded with the product; may be added to or compounded with the product as a liquid by dissolving it in an alcohol or in a polyhydric alcohol such as propylene glycol and glycerin; may be added to or compounded with the product as a solubilized or dispersed liquid by solubilizing or emulsifying the components using a natural gum such as gum Arabic or tragacanth gum, or a surfactant, for example, a nonionic surfactant such as glycerin fatty acid ester and sucrose fatty acid ester, an anionic surfactant, a cationic surfactant or an amphoteric surfactant; may be added to or compounded with the product as a powder coated with a film using a natural gum such as gum Arabic or an excipient such as gelatin and dextrin; or may be added to or compounded with the product as microcapsules by treating with a capsulating agent, depending on the kind of the product to be endowed with cooling sensation, warming and/or pungent sensation or sensory stimulating sensation, or on the final form of the product, for example, liquid, solid, powder, gel, mist or aerosol form. The composition may also be used by being stabilized as a sustained release form by being included into an includant such as cyclodextrin.

The amount of addition or compounding of the cooling sensation agent composition, warming and/or pungent composition or sensory stimulant composition to the product for imparting cooling sensation, warming and/or pungent sensation or sensory stimulating sensation to the product may be adjusted depending on the kind and form of the product, or depending on the cooling sensation effect, warming and/or pungent sensation effect or sensory stimulating effect or function which is desired for the product. For example, the additional or compounding amount of the flavor and fragrance composition of the invention is preferably from about $1 \times 10^{-7}$ to 0.1% by weight generally, more preferably from about $1 \times 10^{-6}$ to 0.01% by weight to the weight of the product added or compounded. The additional or compounding amount of the cooling sensation agent composition, warming and/or pungent agent composition or sensory stimulant composition may be approximately equal range to that of the additional or compounding amount of the flavor and fragrance composition.

EXAMPLES

Hereinafter, the invention will be described in more detail with reference to a synthesis example and examples that, however, do not limit the invention in any way. The examples may be modified within a scope not deviated from the scope of the invention.

Devices and apparatuses for determining physical properties of products obtained in the synthesis example and examples are as follows.

Melting point: Melting point measuring apparatus "MP-S3" (trade name) manufactured by Yanagimoto Co.

Nuclear magnetic resonance spectrum:
$^1$H-NMR; NMR spectrometer "AM-400" (400 MHz) (trade name) manufactured by Bruker Japan Co., Ltd.
External standard substance: tetramethylsilane
Infrared absorption spectrum (IR): IR absorption spectrometer "AVATAR 360 FT-IR" (trade name) manufactured by Nicolet Inc.
Mass spectrum (MS): Mass spectrometer "GCMS-QP2010" (trade name) manufactured by Shimadzu Corporation Synthesis Example 1

Synthesis of (1R,2R,4R)-1-(2-hydroxy-4-methylcyclohexyl)ethanone

To a 500 ml reaction vessel, 70.0 g (453.8 mmol) of isopulegol and 140 ml of methanol were added and ozone generated in an oxygen stream by silent discharge was introduced into the reaction solution while the temperature of the solution was being kept between from 15° C. to 23° C. After 10 hours, disappearance of the raw material, isopulegol was confirmed by the gas chromatogram. The reaction solution obtained was cooled in an ice bath and then added into an excess amount of an aqueous sodium sulfite solution at a temperature of 30° C. or lower, followed by stirring for 2 hours. The solution was extracted with toluene. The toluene solution obtained was sequentially washed with dilute hydrochloric acid, an aqueous sodium carbonate solution, an aqueous ammonium chloride solution and brine, and was dried over anhydrous sodium sulfate. After filtration, the solvent was removed by evaporation under a reduced pressure. The mixture obtained was crystallized by adding 350 ml of heptane, and the crystal obtained was washed with 50 ml of cold heptane followed by drying under vacuum to obtain 53.08 g (yield: 74.9%) of the titled compound as a colorless needle crystal.

Melting point: 46 to 46.5° C.
$^1$H-NMR (500 MHz, CDCl$_3$, δ) ppm: 0.92 (d, J=7.9 Hz, 3H), 0.88-1.04 (m, 2H), 1.22-1.33 (m, 1H), 1.40-1.54 (m, 1H), 1.68-1.76 (m, 1H), 1.93-2.03 (m, 2H), 2.20 (s, 3H), 2.30 (dt, J=3.8 Hz, J=11.2 Hz, 1H), 2.71 (d, J=3.8 Hz, 1H), 4.77-4.87 (m, 1 H).
IR (KBr) cm$^{-1}$: 3346, 3279, 2996, 2961, 2948, 2922, 2867, 2848, 2707, 1471, 1420, 1370, 1352, 1315, 1305, 1268, 1249, 1179, 1132, 1093, 1053, 1018, 960, 944, 844.
MS (m/e): 156 (M$^+$), 138, 123, 110, 95, 81, 71, 67, 55 4 3, 41, 37.

Example 1

Sensory Evaluation

Oral evaluation of an aqueous solution of (1R,2R,4R)-1-(2-hydroxy-4-methylcyclohexyl)ethanone obtained in Synthesis Example 1 was carried out by seven expert panelists. The results of the oral evaluation were as follows.

Odor-quality: acetophenone-like odor with sweetness.
Cool and refreshing feeling of the aqueous solution: cool and refreshing feeling equivalent to 10 ppm of menthol at a concentration of 50 ppm; appearance of refreshing feeling is relatively rapid with clear refreshing feeling without unpleasant taste.

Example 2

Synergetic Effect with Menthol

1-Menthol and (1R,2R,4R)-1-(2-hydroxy-4-methylcyclohexyl)ethanone obtained in Synthesis Example 1 were mixed in ratios of 100:0 to 0:100, and the synergetic effects concerning a cool and refreshing feeling of the mixtures were investigated.

As a result, the 70:30 mixture of l-menthol and (1R,2R,4R)-1-(2-hydroxy-4-methylcyclohexyl)ethanone showed about 40% stronger cool and refreshing feeling than that of menthol alone.

As obvious from Examples 1 and 2, the evaluations for (1R,2R,4R)-1-(2-hydroxy-4-methylcyclohexyl)ethanone alone and the mixture thereof with menthol were both quite excellent.

Example 3

Body Shampoo

A fragrance composition was prepared from 35 parts of (1R,2R,4R)-1-(2-hydroxy-4-methylcyclohexyl)ethanone obtained in Synthesis Example 1 and 65 parts of a fragrance preparation having citrus herbal sense (manufactured by TAKASAGO INTERNATIONAL CORPORATION). A body shampoo was prepared by using the above fragrance composition according to the prescription below. In the prescription, the amounts of compounding are based on "parts by weight".

The shampoo obtained was evaluated with respect to a cooling sensation effect and a lasting of a cooling sensation by body washing of ten common panelists of age 20 to 40 using each 5 g of the body shampoo prepared above. As a result, all of the ten panelists replies that the shampoo gave the cooling sensation and the cooling sensation effect lasted.

<Prescription of body shampoo>

| Components | Amount |
|---|---|
| Triethanolamine | 9.00 |
| Lauric acid | 6.00 |
| Myristic acid | 9.00 |
| Lauryl polyoxyethylenesulfosuccinate disodium salt (1 E.O.) (42%) | 10.00 |
| Alkyl(C8-16) glucoxide | 8.00 |
| Glyceryl laurate | 1.00 |
| 2-hydroxyethyl distearate | 2.50 |
| Coconut oil fatty acid diethanol amide | 3.00 |
| Propylene glycol | 5.00 |
| Dibutylhydroxytoluene | 0.05 |
| Edetic acid disodium salt | 0.10 |
| Ethyl p-oxybenzoate | 0.20 |
| Methyl p-oxybenzoate | 0.10 |
| Fragrance composition | 0.95 |
| Purified water | balance |
| Total | 100.00 |

Example 4

Fragrance Composition

The fragrance composition of Example 4 was prepared by the conventional method according to the prescription below. In the prescription, the amount of compounding is based on "parts by mass".

<Prescription of fragrance composition>

| Components | Amount |
|---|---|
| Apple base (manufactured by TAKASAGO INTERNATIONAL CORPORATION) | 8.0 |
| Bergamot oil | 14.0 |
| Ethyl acetoacetate | 5.0 |
| Methyl dihydrojasmonate | 23.0 |
| Laurinal | 3.0 |
| Levosandol (manufactured by TAKASAGO INTERNATIONAL CORPORATION) | 4.0 |
| Orange oil | 8.0 |
| 10-oxa-16-hexadecanoride | 8.0 |
| Phenoxanol (manufactured by IFF Inc.) | 6.0 |
| Styrallyl acetate | 3.0 |
| Tesalon (manufactured by TAKASAGO INTERNATIONAL CORPORATION) | 8.0 |
| (1R,2R,4R)-1-(2-hydroxy-4-methylcyclohexyl)ethanone | 30.0 |

Example 5

Shampoo

According to the prescription below, the shampoo (100 g) of Example 5 endowed with 1% of the fragrance composition of Example 4 was prepared.

The shampoo obtained was evaluated with respect to a cooling sensation effect and a lasting of a cooling sensation by hair washing of ten common panelists of age 20 to 40 using each 5 g of the shampoo. As a result, all of the ten panelists replied that the shampoo gave the cooling sensation and the cooling sensation effect lasted.

<Prescription of shampoo>

| Components | Amount(g) |
|---|---|
| Sodium polyoxyethylene lauryl ether sulfate | 14.00 |
| Lauric acid amide propyl betaine | 4.00 |
| Coconut oil fatty acid diethanol amide | 3.00 |
| Cationic cellulose | 0.50 |
| Ethylene glycol distearate | 1.00 |
| Ethyl p-oxybenzoate | 0.25 |
| Citric acid | proper quantity |
| Fragrance composition | 1.00 |
| Purified water | balance |
| Total | 100.00 |

Example 6

Clear Shampoo

The clear shampoo was prepared according to the prescription below.

The clear shampoo obtained was evaluated with respect to a cooling sensation effect and a lasting of a cool sensation by hair washing of ten common panelists of age 20 to 40 using each 5 g of the shampoo. As a result, all of the ten panelists replied that the shampoo gave the cooling sensation and the cooling sensation effect lasted.

| <Prescription of transparent shampoo> | |
|---|---|
| Components | Amount(g) |
| Polyquaternium 10 | 10.0 |
| Sodium laureth sulfate (aqueous 30% solution) | 300.0 |
| Lauroylsarcosine sodium salt (aqueous 30% solution) | 50.0 |
| Cocamide propene betaine | 100.0 |
| Coconut fatty acid diethanol amide | 40.0 |
| 1,3-butylene glycol | 20.0 |
| Citric acid | 3.0 |
| Methylparaben | 2.0 |
| Propylparaben | 0.5 |
| Edetic acid disodium salt | 1.0 |
| l-menthol | 6.3 |
| (1R,2R,4R)-1-(2-hydroxy-4-methylcyclohexyl)ethanone | 0.6 |
| Vanillyl butyl ether | 0.1 |
| Citrus type fragrance | 3.0 |
| Purified water | balance |
| Total | 1000.0 |

Example 7

Toothpaste

The toothpaste was prepared according to the prescription below.

The tooth paste obtained was evaluated with respect to a cooling sensation effect and a lasting of a cool sensation by tooth brushing of ten common panelists of age 20 to 40 with each 2 g of the toothpaste. As a result, all of the 10 panelists replied that the toothpaste gave the cooling sensation and the cooling sensation effect lasted.

| <Prescription of tooth paste> | |
|---|---|
| Components | Amount(g) |
| l-Menthol | 0.25 |
| (1R,2R,4R)-1-(2-hydroxy-4-methylcyclohexyl)ethanone | 0.25 |
| Calcium hydrogen phosphate (dihydrate) | 50.00 |
| Glycerin | 25.00 |
| Sodium lauryl sulfate | 1.40 |
| Carboxymethyl cellulose sodium salt | 1.50 |
| Saccharin sodium salt | 0.20 |
| Sodium benzoate | 0.10 |
| Strawberry type flavor (manufactured by TAKASAGO INTERNATIONAL CORPORATION) | 0.70 |
| Purified water | balance |
| Total | 100.00 |

Example 8

Peach Flavor

Peach flavor was prepared according to the prescription below. A soft sweetness was newly endowed with the flavor by addition of (1R,2R,4R)-1-(2-hydroxy-4-methylcyclohexyl)ethanone and mildness of peach could be realized thereby.

| <Prescription of peach flavor> | |
|---|---|
| Components | Amount(g) |
| Benzaldehyde | 0.2 |
| (1R,2R,4R)-1-(2-hydroxy-4-methyl cyclohexyl)ethanone | 0.2 |
| Cis-3-hexenol | 0.3 |
| Ethyl acetate | 2.0 |
| Ethyl butyrate | 0.8 |
| Ethyl maltol | 0.3 |
| γ-Undeca lactone | 0.5 |
| Linalool | 0.5 |
| Trans-2-hexenol | 0.6 |
| Peach flavor base (manufactured by TAKASAGO INTERNATIONAL CORPORATION) | 5.0 |
| Ethyl alcohol | balance |
| Total | 100.00 |

Example 9

Green Tea Flavor

Green tea flavor was prepared according to the prescription below. A soft maturation was newly endowed with the flavor by addition of (1R,2R,4R)-1-(2-hydroxy-4-methylcyclohexyl)ethanone and fragrant smell of the green tea could be realized thereby.

| <Prescription of green tea flavor> | |
|---|---|
| Components | Amount(g) |
| Benzyl alcohol | 1.0 |
| (1R,2R,4R)-1-(2-hydroxy-4-methylcyclohexyl)ethanone | 0.3 |
| Cis-3-hexenol | 0.3 |
| Dimethyl sulfide | 0.1 |
| Geraniol | 0.6 |
| l-Menthol | 0.4 |
| Linalool | 2.5 |
| Nerolidol | 0.9 |
| Terpineol | 0.2 |
| Green tea base | 5.0 |
| Ethyl alcohol | balance |
| Total | 100.00 |

Example 10

Black Tea Flavor

Black tea flavor was prepared according to the prescription below. A soft sweetness was newly endowed with the flavor by addition of (1R,2R,4R)-1-(2-hydroxy-4-methylcyclohexyl)ethanone and mildness of the black tea could be realized thereby.

| <Prescription of black tea flavor> | |
|---|---|
| Components | Amount(g) |
| α-Ionone | 0.2 |
| β-Ionone | 0.2 |
| Benzaldehyde | 1.0 |
| (1R,2R,4R)-1-(2-hydroxy-4-methylcyclohexyl)ethanone | 1.0 |
| Cis-3-hexenol | 6.0 |
| δ-Decalactone | 2.5 |
| δ-Dodecalactone | 2.0 |
| Damascenone | 0.1 |
| Linalool | 3.5 |
| Geraniol | 6.0 |
| Citral | 1.0 |
| Linalool oxide | 1.6 |
| Methyl salicylate | 2.0 |
| Phenylethyl alcohol | 6.0 |
| Hexyl aldehyde | 1.0 |
| Propylene glycol | balance |
| Total | 100.00 |

Example 11

Tobacco Flavor Composition

A tobacco flavor composition was prepared according to the prescription below. When a commercially available tobacco was flavored with 0.1% of the tobacco flavor composition containing (1R,2R,4R)-1-(2-hydroxy-4-methylcyclohexyl)ethanone, mild feeling was imparted to the smoke from the tobacco and a tobacco-like flavor or an emphatic tobacco-like flavor was also imparted to the tobacco.

| <Prescription of tobacco flavor composition> | |
|---|---|
| Components | Amount(g) |
| l-Menthol | 2.00 |
| Vanillin | 1.40 |
| Heliotropine | 2.00 |
| Ethyl oxyhydrate | 0.80 |
| Ethyl butyrate | 0.25 |
| Ethyl valerianate | 0.25 |
| Linalool | 0.30 |
| Geraniol | 0.40 |
| Anethole | 1.60 |
| γ-Valerolactone | 0.80 |
| Cedarwood oil | 2.30 |
| Chamomile oil | 0.20 |
| Fennel oil | 0.20 |
| (1R,2R,4R)-1-(2-hydroxy-4-methylcyclohexyl)ethanone | 1.00 |
| Ethyl alcohol | balance |
| Total | 100.00 |

The invention claimed is:

1. A flavor and fragrance composition comprising 1-(2-hydroxy-4-methylcyclohexyl)ethanone represented by the formula (1):

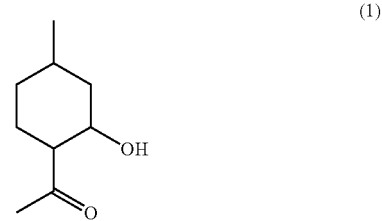

(1)

and one or more selected from the group consisting of menthol, menthone, camphor, pulegol, cineol, mint oil, peppermint oil, spearmint oil, eucalyptus oil, 3-1-menthoxypropane-1,2-diol, N-alkyl-p-menthane-3-carboxamide, 3-1-menthoxy-2-methylpropane-1,2-diol, p-menthane-3,8-diol, 2-1-menthoxyethane-1-ol, 3-1-menthoxypropane-1-ol, 4-1-menthoxybutane-1-ol, menthyl 3- hydroxybutanoate, menthyl lactate, menthone glycerin ketal, 2-(2-1-menthyloxyethyl)ethanol, menthyl glyoxylate, N-methyl-2,2-isopropylmethyl-3-methylbutanamide, menthyl 2-pyrrolidone-5-carboxylate, monomenthyl succinate, alkali metal salts of monomenthyl succinate, and alkali earth metal salts of monomenthyl succinate, monomenthyl glutarate, alkali metal salts of monomenthyl glutarate, alkali earth metal salts of monomenthyl glutarate, N-[[5-methyl-2-(1-methylethyl)-cyclohexyl]carbonyl]glycine, p-menthane-3-carboxylic acid glycerol ester, Menthol propylene glycol carbonate; menthol ethylene glycol carbonate, and 6-isopropyl-3,9-dimethyl-1,4-dioxaspiro[4.5]decan-2-one.

2. The flavor and fragrance composition according to claim 1, wherein the 1-(2-hydroxy-4-methylcyclohexyl)-ethanone represented by the above formula (1) is a (1R,2R,4R)-stereoisomer compound represented by the following formula (1-a):

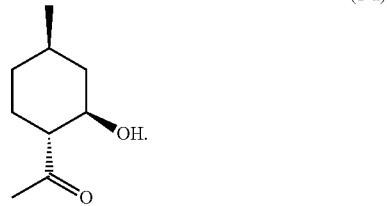

(1-a)

3. The flavor and fragrance composition according to claim 1 or 2, wherein the flavor and fragrance composition has a cooling sensation effect.

4. A flavor and fragrance composition comprising 1-(2-hydroxy-4-methylcyclohexyl)ethanone represented by the formula (1):

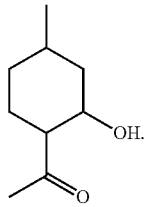

(1)

and at least one of warming and/or pungent agents.

5. The flavor and fragrance composition according to claim 4, wherein the warming and/or pungent agents are vanillylethyl ether, vanillylpropyl ether, vanillin propylene glycol acetal, ethylvanillin propylene glycol acetal, capsaicin, gingerol, vanillylbutyl ether, vanillylbutyl ether acetate, 4-(1-menthoxymethyl)-2-phenyl-1,3-dioxolane, 4-(1-menthoxymethyl)-2-(3',4'-dihydroxyphenyl)-1,3-dioxolane, 4-(1-menthoxymethyl)-2-(2'-hydroxy-3'-methoxyphenyl)-1,3-dioxolane, 4-(1-menthoxymethyl)-2-(4'-methoxyphenyl)-1,3-dioxolane, 4-(1-menthoxymethyl)-2-(3',4'-methylenedioxyphenyl)-1,3-dioxolane, 4-(1-methoxymethyl)-2-(3'-methoxy-4'-hydroxyphenyl)-1,3-dioxolane, red pepper oil, red pepper oleoresin, ginger oleoresin, nonylic acid vanillamide, jambu oleoresin, Japanese pepper extract, sanshool-I, sanshool-II, sanshoamide, black pepper extract, chavicine, piperine, and spilanthol.

6. A beverage or food product, a fragrance or cosmetic product, a daily utensil product, an oral composition, or a pharmaceutical product, wherein 0.0001 to 20% by weight of the flavor and fragrance composition according to claim 1 or 4 is compounded.

7. A method of producing a beverage or food product, a fragrance or cosmetic product, a daily utensil product, an oral composition, or a pharmaceutical product, wherein the flavor and fragrance composition according to claim 1 or 4 is added to the beverage or food product, fragrance or cosmetic product, daily utensil product, oral composition, or pharmaceutical product.

8. The flavor and fragrance composition according to claim 4, wherein the 1-(2-hydroxy-4-methylcyclohexyl)-ethanone represented by the above formula (1) is a (1 R,2R,4R)-stereoisomer compound represented by the following formula (1-a):

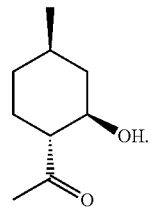

(1-a)

9. The flavor and fragrance composition according to claim 4 or 8, wherein the flavor and fragrance composition has a cooling sensation effect.

10. The flavor and fragrance composition according to claim 9, further comprising at least one cooling sensation agent not included in the compounds represented by the above formula (1).

11. The flavor and fragrance composition according to claim 10, wherein the cooling sensation agent not included in the compounds represented by the above formula (1) is one or more selected from the group consisting of menthol, menthone, camphor, pulegol, isopulegol, cineol, mint oil, peppermint oil, spearmint oil, eucalyptus oil, 3-1-menthoxypropane -1,2-diol, N-alkyl-p-menthane-3-carboxamide, 3-1-menthoxy-2-methylpropane-1,2-diol, p-menthane-3,8-diol, 2-1-menthoxyethane-1-ol, 3-1-menthoxypropane-1-ol, 4-1-menthoxybutane-1-ol, menthyl 3- hydroxybutanoate, menthyl lactate, menthone glycerin ketal, 2-(2-1-menthyloxyethyl)ethanol, menthyl glyoxylate, N-methyl-2,2-isopropylmethyl-3-methylbutanamide, menthyl 2-pyrrolidone-5-carboxylate, monomenthyl succinate, alkali metal salts of monomenthyl succinate, and alkali earth metal salts of monomenthyl succinate, monomenthyl glutarate, alkali metal salts of monomenthyl glutarate, alkali earth metal salts of monomenthyl glutarate, N-[[5-methyl-2-(1-methylethyl)-cyclohexyl]carbonyl]glycine, p-menthane-3-carboxylic acid glycerol ester, menthol propylene glycol carbonate; menthol ethylene glycol carbonate, and 6-isopropyl-3,9-dimethyl-1,4-dioxaspiro[4.5]decan-2-one.

* * * * *

UNITED STATES PATENT AND TRADEMARK OFFICE
CERTIFICATE OF CORRECTION

| | |
|---|---|
| PATENT NO. | : 8,071,531 B2 |
| APPLICATION NO. | : 11/922208 |
| DATED | : December 6, 2011 |
| INVENTOR(S) | : Takashi Aida et al. |

It is certified that error appears in the above-identified patent and that said Letters Patent is hereby corrected as shown below:

On the title page, item (73), **Specifically, please correct the typographical error found in the name of the Assignee:
~~TAKASGO~~ TAKASAGO INTERNATIONAL CORPORATION, TOKYO (JP)**

Signed and Sealed this
Twelfth Day of March, 2013

Teresa Stanek Rea
*Acting Director of the United States Patent and Trademark Office*